(12) United States Patent
Grooms et al.

(10) Patent No.: US 6,290,718 B1
(45) Date of Patent: Sep. 18, 2001

(54) LUMINAL GRAFT, STENT OR CONDUIT MADE OF CORTICAL BONE

(75) Inventors: Jamie M. Grooms, Alachua; Russell S. Donda, Gainesville, both of FL (US)

(73) Assignee: Regeneration Technologies, Inc., Alachua, FL (US)

( * ) Notice: Subject to any disclaimer, the term of this patent is extended or adjusted under 35 U.S.C. 154(b) by 0 days.

(21) Appl. No.: 09/017,472

(22) Filed: Feb. 2, 1998

(51) Int. Cl.$^7$ ........................................ A61F 2/06
(52) U.S. Cl. ................................. 623/1; 623/12; 623/16
(58) Field of Search .................... 623/1, 12, 16

(56) References Cited

U.S. PATENT DOCUMENTS

| | | |
|---|---|---|
| 3,284,557 | 11/1966 | Polansky . |
| 4,597,762 | 7/1986 | Walter et al. . |
| 4,787,900 | 11/1988 | Yannas . |
| 4,923,380 | 5/1990 | Huc et al. . |
| 4,932,973 | 6/1990 | Gendler . |
| 4,963,146 | 10/1990 | Li . |
| 5,019,087 | 5/1991 | Nichols . |
| 5,026,381 | 6/1991 | Li . |
| 5,037,377 | 8/1991 | Alonso . |
| 5,053,049 | 10/1991 | Campbell . |
| 5,112,354 * | 5/1992 | Sires ........................................ 623/16 |
| 5,139,505 | 8/1992 | Palmieri . |
| 5,152,791 * | 10/1992 | Hakamatsuka et al. ................ 623/16 |
| 5,171,273 | 12/1992 | Silver et al. . |
| 5,192,311 | 3/1993 | King et al. . |
| 5,246,451 * | 9/1993 | Trescony et al. ........................ 623/1 |
| 5,376,110 | 12/1994 | Tu et al. . |
| 5,507,813 | 4/1996 | Dowd et al. . |
| 5,549,664 | 8/1996 | Hirata et al. . |
| 5,591,225 | 1/1997 | Okuda . |
| 5,613,982 | 3/1997 | Goldstein . |
| 5,632,778 | 5/1997 | Goldstein . |
| 5,665,116 | 9/1997 | Chaisson et al. . |
| 5,676,146 | 10/1997 | Scarborough . |
| 5,899,939 * | 5/1999 | Boyce et al. ........................... 623/16 |

FOREIGN PATENT DOCUMENTS 0 483 944    5/1992   (EP) .

* cited by examiner

*Primary Examiner*—David H. Willse
*Assistant Examiner*—Suzette J. Jackson
(74) *Attorney, Agent, or Firm*—Bencen & Van Dyke, P.A; Gerard H. Bencen; Timothy H. Van Dyke

(57) ABSTRACT

This invention relates to implants useful as stents for opening or strengthening biological conduits, or as grafts or conduits for replacing or connecting portions of biological tissues having a lumen. Accordingly, the implants of this invention may be applied in portions of the peripheral and coronary vascular system, biliary, urinary, esophageal, digestive, ocular, tracheal, bronchial, reproductive, and neural systems. The implant comprises a segment of bone having a lumen through at least a part thereof, and wherein at least a portion of the implant is demineralized so as to be pliable.

21 Claims, 9 Drawing Sheets

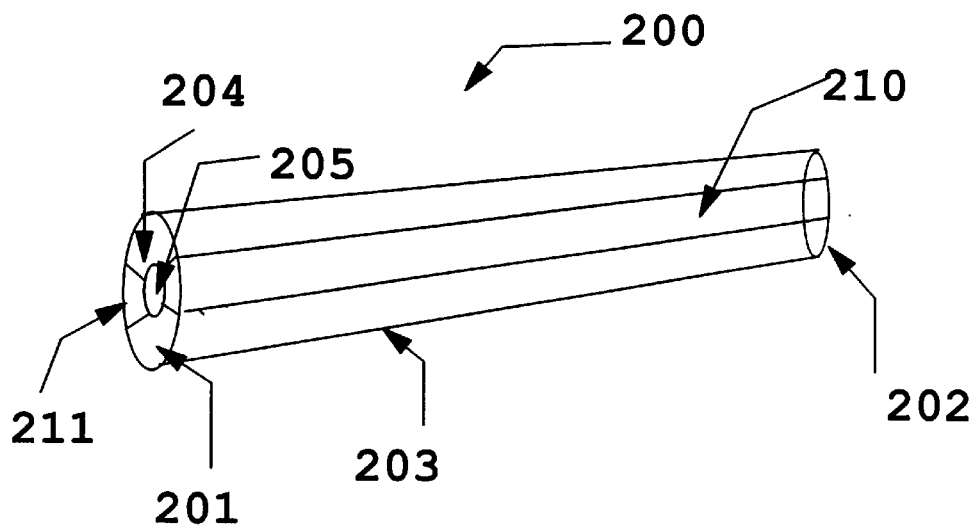
Fig. 2A
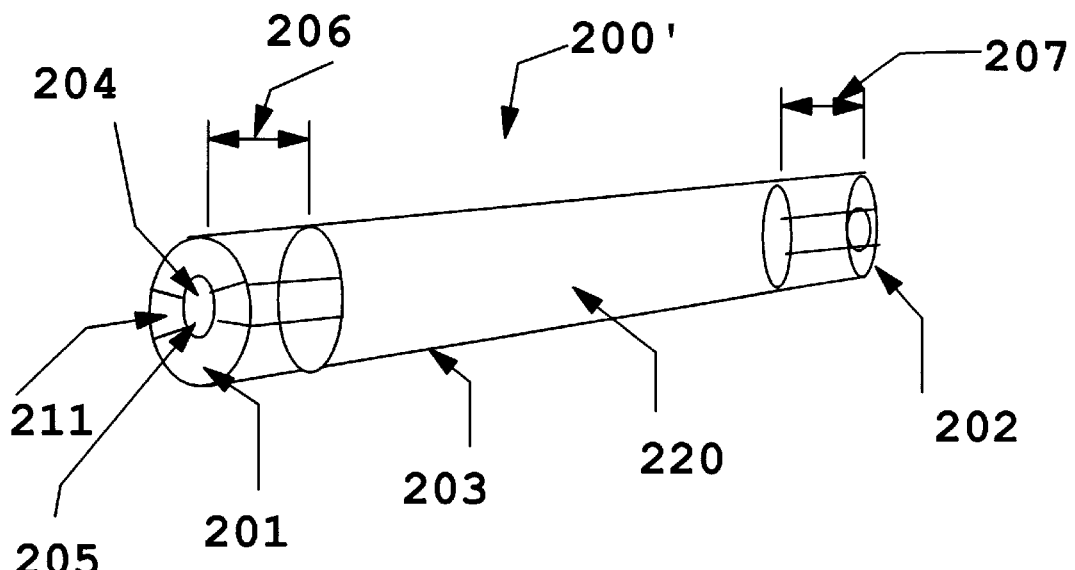
Fig. 2B
Figure 2

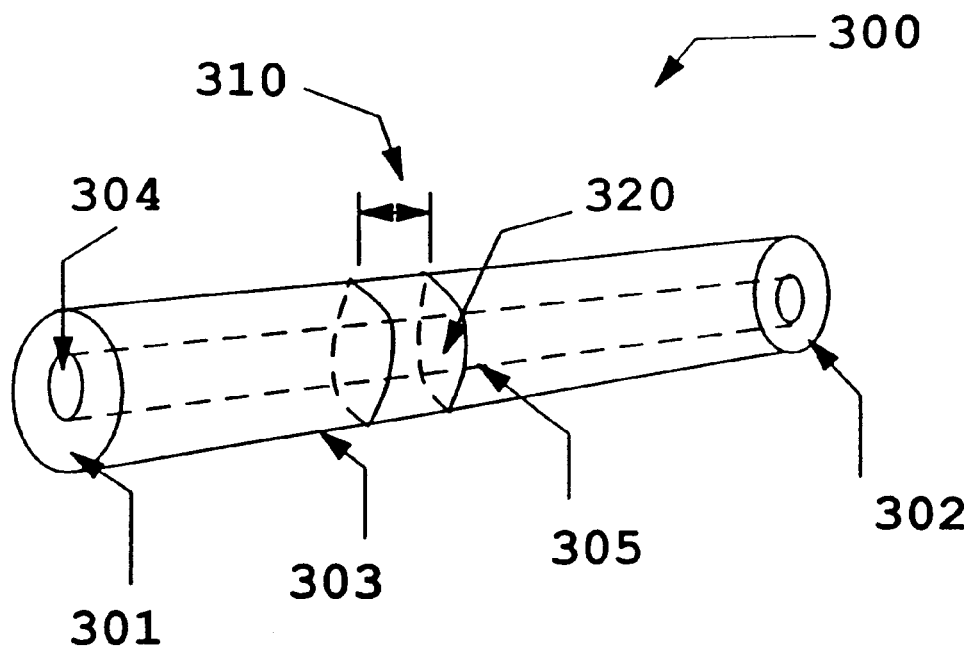
Fig. 3A
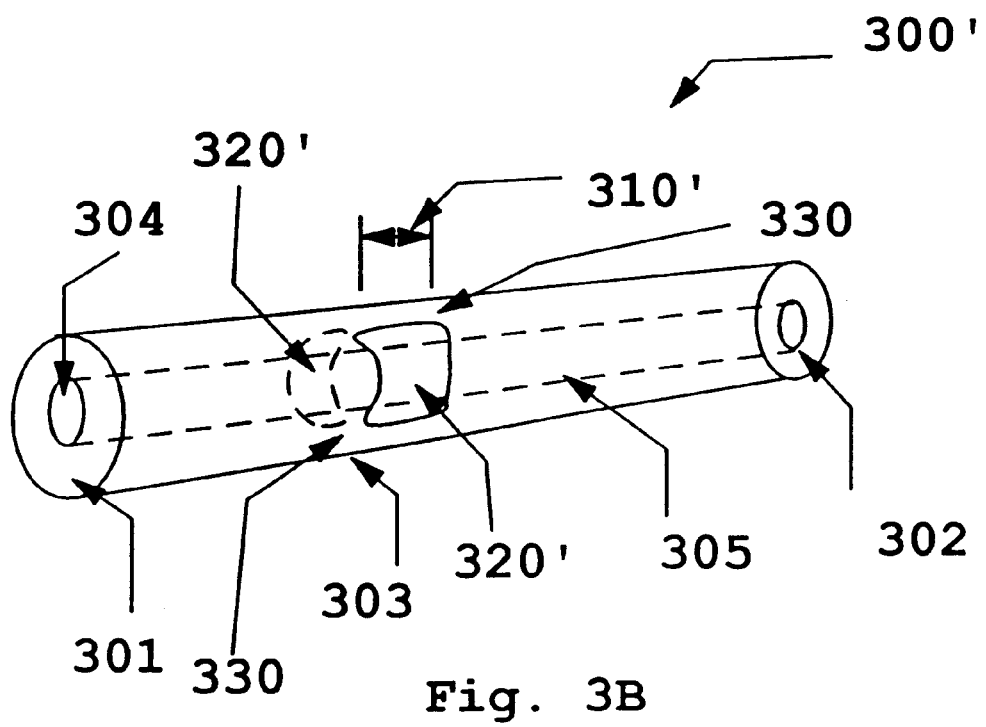
Fig. 3B
Figure 3

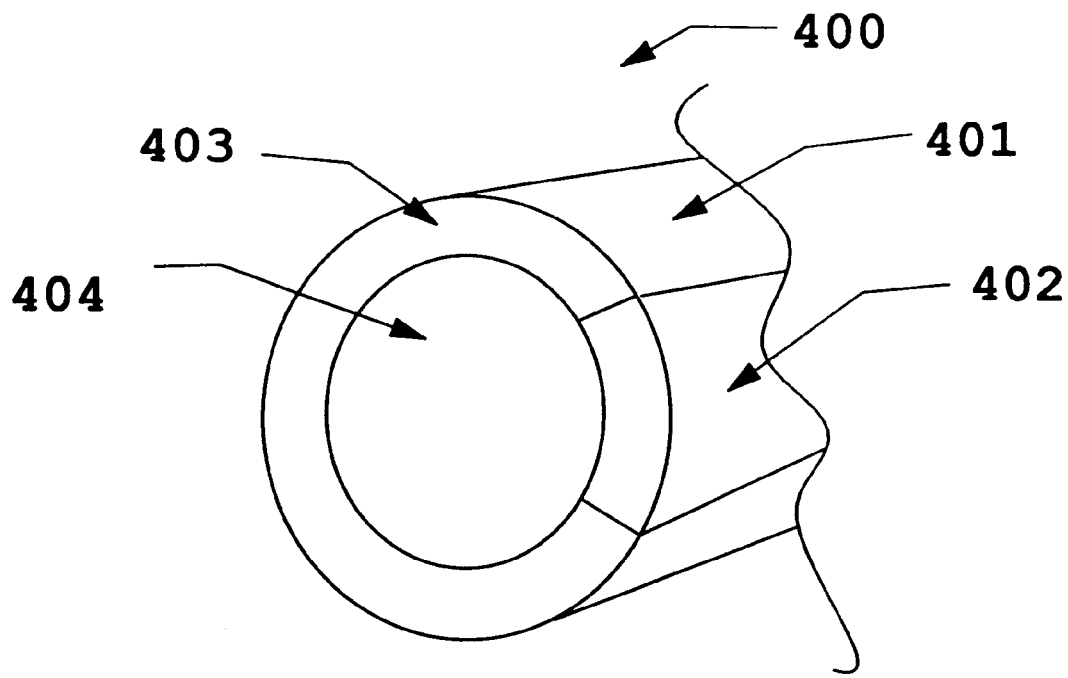
Fig. 4A
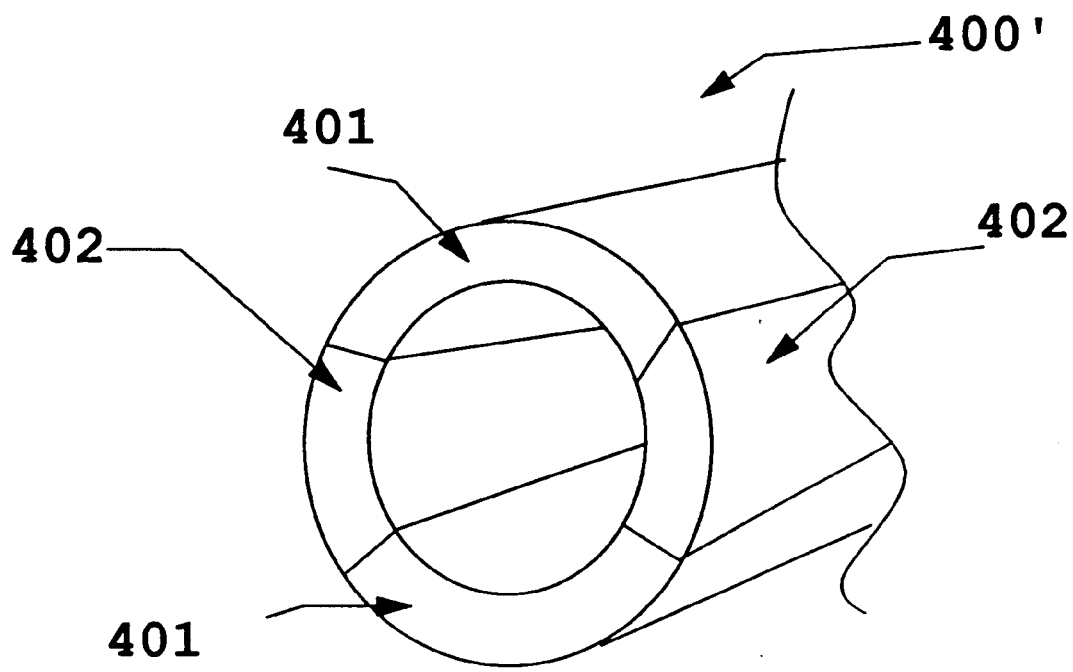
Fig. 4B
Figure 4

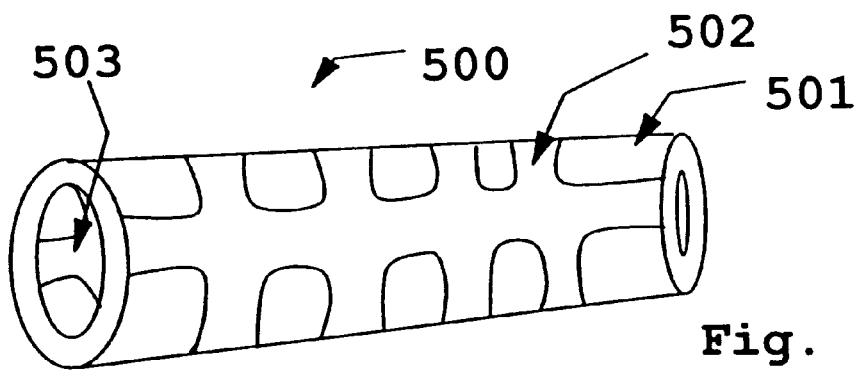
Fig. 5A
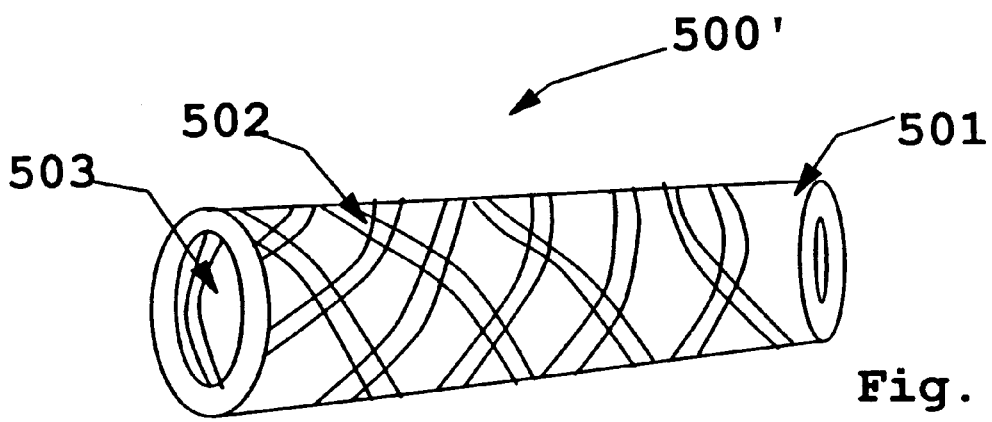
Fig. 5B
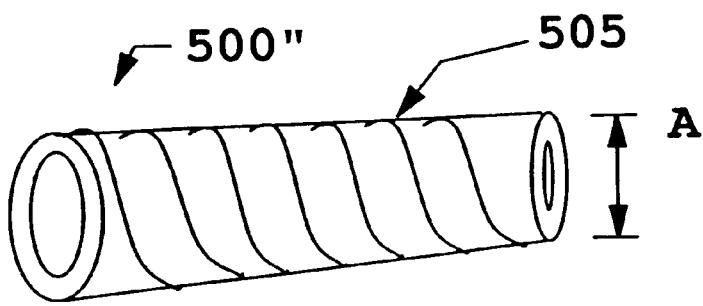
Fig. 5C
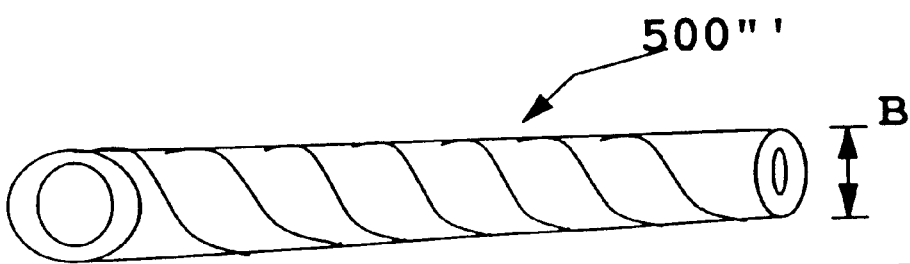
Fig. 5D
Figure 5

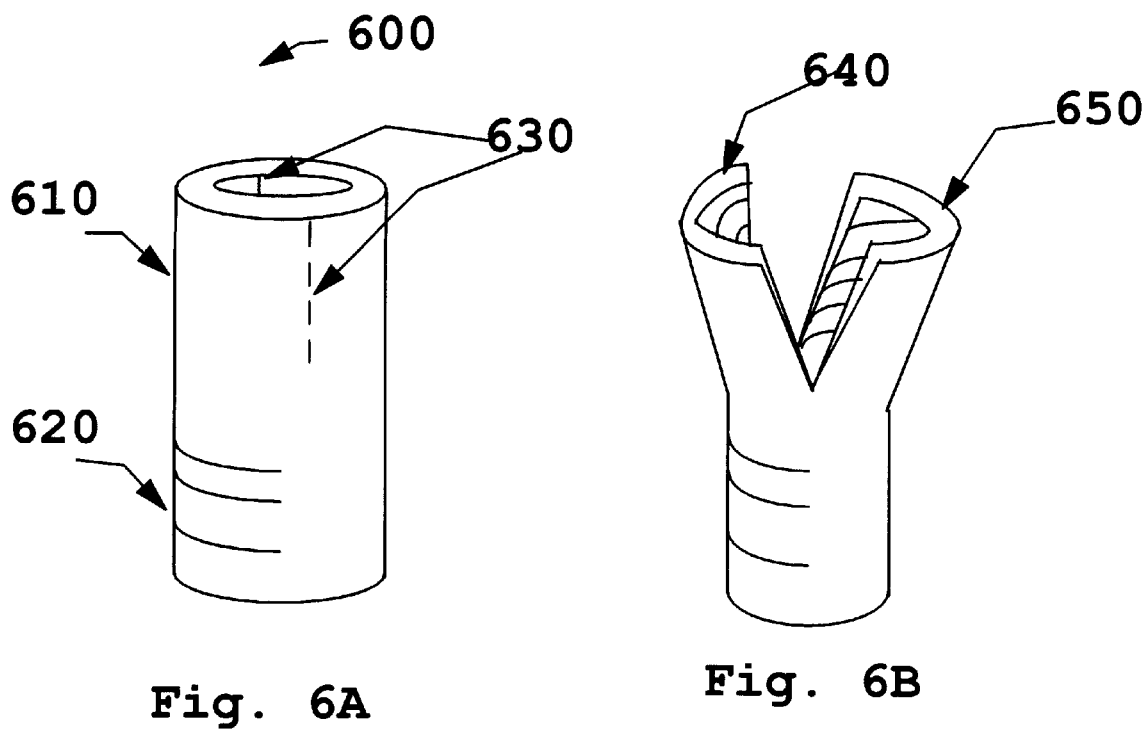
Fig. 6A
Fig. 6B
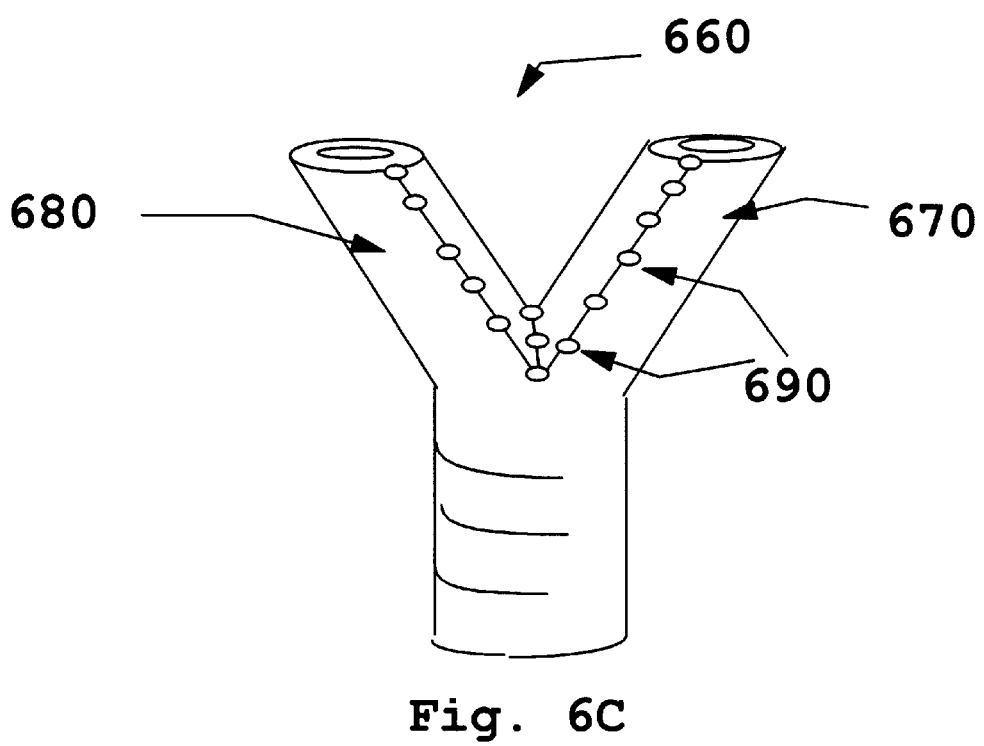
Fig. 6C
Figure 6

LUMINAL GRAFT, STENT OR CONDUIT MADE OF CORTICAL BONE

BACKGROUND OF THE INVENTION

1. Field of the Invention

This invention relates to a novel intraluminal graft, stent, or conduit implant produced by demineralization of cortical bone having a lumen, appropriate shape and dimensions.

2. Background

In the field of vascular transplantation, many devices are known for opening an occluded vessel, as with a stent, or for replacing or strengthening portions of a vessel, as in bypass surgery. Various synthetic conduits for use in physiologic locations where production of a passage is desired have also been described. However, such methods typically depend on insertion into the biological milieu of a synthetic device, which typically requires removal at a later date, harvesting of autograft or allograft tissue from limited resource sites, or production of complex mixtures for preparation of the desired conduit or implant.

Examples of know methods for producing grafts, stents or conduits include the following:

A. Grafts

U.S. Pat. No. 5,376,110 discloses a chemically cross-linked collagenous graft material wherein physical force, stress or movement is applied during a collagen cross-linking process in order to derive desired shapes.

U.S. Pat. No. 5,192,311 discloses a method for making a homograft wherein a tubular substrate having a thrombogenic surface is implanted in a blood vessel in order to permit collagenous growth to occur on the thrombogenic surface to form a vessel which is then removed from the substrate and used as a graft material.

U.S. Pat. No. 4,787,900 discloses a method for making an inner layer of a multilayer blood vessel prosthesis by contacting collagen with an aminopolysaccharide and crosslinking the resulting polymer, and forming an outer layer by freeze-drying bioreplaceable material onto the inner layer.

U.S. Pat. No. 5,591,225 discloses an artificial blood vessel comprising a tube of a porous synthetic polymer on which a protein or peptide having cell adhesion and growth functions is covalently bonded to encourage cellular adhesion and to prevent thrombus formation.

U.S. Pat. No. 5,549,664 discloses an artificial blood vessel made from an elastomeric material wherein a first layer has closed, noncommunicating cells, and a second layer thereof has open, mutually communicating cells.

U.S. Pat. No. 5,037,377 discloses a method for improving the biocompatibility of a vascular graft by using collagen to coat a biocompatible fabric which is to be contacted with blood, and then cross-linking the collagen coating.

U.S. Pat. No. 3,284,557 discloses a method for "crimping" a tube of collagen for use as a vascular prosthesis, so that when bent, the collagen tube does not kink and thereby become occluded. The collagen tube was woven from "collagen yarn".

B. Stents

U.S. Pat. No. 5,665,116 describes a method and apparatus for catheterization to dilate a vascular blockage wherein a catheter assembly carries a balloon to a site of vascular blockage where the balloon is expanded to uncoil a coiled ring structure having longitudinally extended struts, which is carried on the balloon, and which locks to remain in an uncoiled position to dilate the blocked vessel.

U.S. Pat. Nos. 5,195,984; 5,571,171; 4,776,337; and 5,102,417; disclose various embodiments of balloon catheters for insertion of stents.

C. Conduits

U.S. Pat. Nos. 4,963,146 and 5,026,381 disclose a multi-layered, semi-permeable conduit for nerve regeneration wherein the conduit is prepared by precipitation of an aqueous dispersion of Type 1 collagen and spinning the precipitate to form a conduit which must be further compressed, frozen, lyophilized, and cross-linked, prior to use.

U.S. Pat. No. 5,019,087 discloses a conduit prepared from Type 1 collagen and laminin for nerve regeneration, wherein the collagen and laminin are admixed at defined ratios.

D. Auxiliary Technology

U.S. Pat. Nos. 5,613,982 and 5,632,7798 disclose a method for reducing the immunogenicity of a collagenous implant by removing cells from a tissue to produce a tissue matrix, washing the tissue matrix to remove antigens, and treating with adhesion factors (fibronectin, heparin) to promote attachment of fibroblast cells immunologically acceptable to the intended recipient of the thus prepared implant.

U.S. Pat. No. 4,597,762 discloses a collagen preparation produced by proteolyzing mammalian Type-1 collagen containing material under specific conditions, cross-linking the proteolyzed material, reducing (bleaching) the cross-linked material and sterilizing the reduced material.

U.S. Pat. No. 5,507,813 discloses a shaped material derived from elongate, demineralized, bone particles having specified median lengths, and which are bonded to each other by admixture with adhesives, fillers, plasticizers, and the like.

U.S. Pat. No. 5,676,146 discloses a method for radiologic tracking of an implant, such as that described in U.S. Pat. No. 5,507,813, by including therein a piece of mineralized bone, which acts as a resorbable radiopaque marker.

U.S. Pat. No. 5,171,273 discloses a synthetic tendon comprising aligned, cross-linked, synthetic collagen fibers embedded in a non-crosslinked collagen matrix.

U.S. Pat. No. 4,923,380 discloses a method for preparing collagen tubes for use as a vascular prosthesis or nerve suture wherein aqueous collagen is "coagulated" as it is extruded in a tubular manner, followed by addition of azide, rather than glutaraldehyde, to induce "denaturation" of the collagen.

U.S. Pat. No. 5,139,505 discloses a radiopaque device comprising a collagen tube with frusto-conical ends and an intermediate annular rim for assisting in suturing adjacent hollow organs (intestines, bile ducts, etc.), along with a collagen wrap to be used as a band-aid.

In view of the above art in which various forms of grafts, stents, conduits and auxiliary technology has been described, it will now better be appreciated that the present invention provides a novel device and method for meeting the continuing need for grafts, stents and conduits for biological systems by providing partially or fully demineralized bone segments having a lumen for use in these applications. Any of the known technology, including the above mentioned auxiliary technology, however, may be applied in various embodiments of the present invention in order to, for example, reduce the immunogenicity or thrombogenicity of the present device, and the above discussed art is therefore incorporated by reference for that purpose.

SUMMARY OF THE INVENTION

This invention relates to implants useful as stents for opening or strengthening biological conduits, or as grafts or conduits for replacing or connecting portions of biological tissues having a lumen or in which conduction of material (e.g. as a neural suture) is required. Accordingly, the implants of this invention may be applied in portions of the peripheral and coronary vascular system, ocular, biliary, urinary, renal, esophageal, tracheal, reproductive, and neural systems. The implant comprises a segment of bone having a lumen, machined or naturally occurring, through at least a part thereof, and at least a portion of which is demineralized so as to be pliable.

BRIEF DESCRIPTION OF THE DRAWINGS

FIG. 2 provides a side view of a tubular implant embodiment of this invention comprising a lumen and a body comprised of cortical bone having demineralized longitudinal segments (FIG. 2A) and an embodiment wherein, in addition, an internal segment of the implant is fully demineralized while terminal annular segments of the implant are retained in a relatively rigid, mineralized or partially demineralized state (FIG. 2B). It should be appreciated that for some applications, there may be only one terminal annular segment that is retained in a relatively rigid mineralized or partially demineralized state, and in other embodiments, it may be preferred for the internal segment to be mineralized, with either or both terminal annular segments being demineralized.

FIG. 3 provides a side view of a tubular implant embodiment of this invention comprising a lumen and a body comprised of demineralized cortical bone wherein an annulus thereof, between the termini of the implant, is retained in a relatively rigid, mineralized or partially demineralized state, (FIG. 3A) and an embodiment wherein the annulus of mineralized bone is interrupted by a segment of demineralized bone (FIG. 3B).

FIG. 4 provides a sectional view through a tubular implant embodiment of this invention comprising a lumen and a body comprised of a longitudinal segment of demineralized cortical bone along one longitudinal aspect of the implant (FIG. 4A) and an embodiment comprising two longitudinal segments along two longitudinal aspects of the implant (FIG. 4B).

FIG. 6 provides side views of various stages in the process of preparing a bifurcated implant of this invention by slicing and suturing a demineralized segment of the implant.

DETAILED DESCRIPTION OF THE PREFERRED EMBODIMENTS

Figure 1:
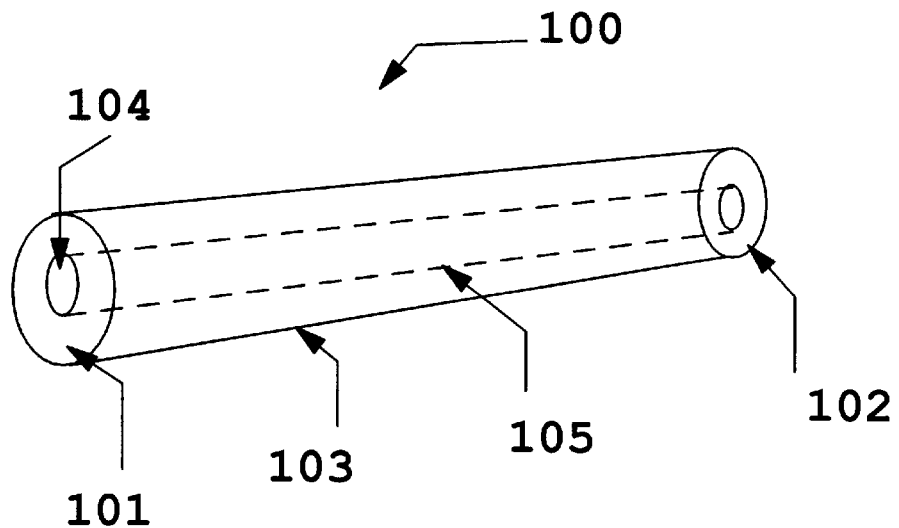
FIG. 1 provides a side view of a tubular implant embodiment of this invention comprising a lumen and a body comprised of uniformly demineralized cortical bone (FIG. 1A) and an embodiment wherein terminal annular segments of the implant are retained in a relatively rigid, mineralized or only partially demineralized state (FIG. 1B). It should be appreciated that for some applications, there may be only one terminal annular segment that is retained in a relatively rigid mineralized or partially demineralized state, and in other embodiments, it may be preferred for the internal segment to be mineralized, with either or both terminal annular segments being demineralized.
Figure 1:
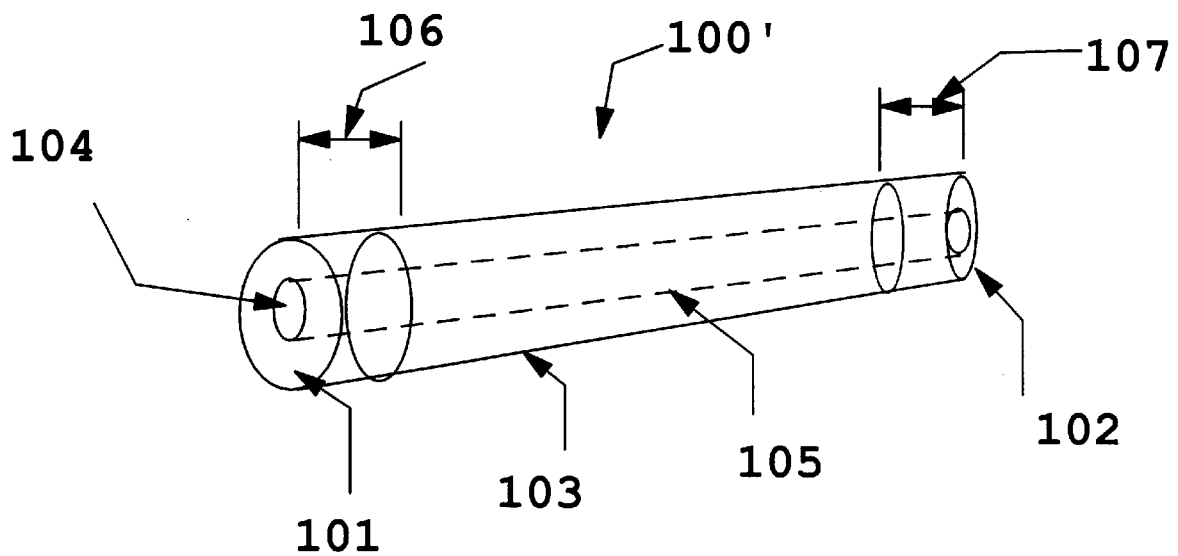

In preferred embodiments of the implant of this invention, the implant comprises a body of cortical bone having a lumen through at least a portion thereof. The lumen has an internal diameter approximately matching the internal diameter of the lumen of a physiologic channel. In addition, preferably, the implant also has an external diameter allowing the implant to be inserted into the lumen of a physiologic channel, or to allow two portions of an existing physiologic channel to be connected to each other. At least a segment of the implant is relatively rigid, due to no or partial demineralization, while another portion of the implant is relatively pliable as a result of that segment having been demineralized or partially demineralized.

The source bone may be of either human (allograft or autograft) or animal origin (xenograft), or it may be derived by culture in vitro or from recombinant bone sources, and may be implanted into humans or animals. Those skilled in the art will recognize that, in addition to bone material, a biocompatible coating or infusate may be incorporated into or onto the implant. Various treatments may be applied to the implant, in order to: (a) reduce antigenicity or immunogenicity, (e.g. "tanning," treatment with glutaraldehyde, urea, other chaotropic agents, see the treatment of U.S. Pat. Nos. 5,613,982; 5,632,778, hereby incorporated by reference, and the like); (b) reduce thrombogenicity, as in treatments with anti-thrombogenic compounds and surface treatments (e.g. by treatment with barium sulfate; see also the treatments of U.S. Pat. Nos. 5,192,311; 4,787,900; 5,591,225; all of which are hereby incorporated by reference herein as potential treatments for the implant of this invention when it is to be applied as an intravascular graft, stent or conduit); (c) impart or retain radiopacity for all or a portion of the implant, to assist in positioning, orientation and tracking of the implant (e.g. see the method of U.S. Pat. No. 5,676,146, and patents mentioned therein, all of which are hereby incorporated by reference for purposes of teaching production of an implant having radiopaque characteristics, bearing in mind, however, the distinction that, per the referenced U.S. Pat. No. 5,676,146 patent, radiopaque native, mineralized bone is added to a composite of demineralized bone particles in which the only purpose of the mineralized bone is to provide a radiopaque marker, while in the present invention, an unitary device is disclosed in which the radiopaque, mineralized portion of the device is an integral part of the implant, and which has a functional, structural role to play, over and above the mere provision of radiopacity).

It will further be appreciated that the dimensions of the implant of this invention will be dictated by the dimensions of the implant site. For example, the implant may desirably have an internal diameter of between about 2 millimeters (e.g. for a coronary artery implantation site) to about 40 millimeters (e.g. for an aortic implantation site), with internal diameters anywhere between these extremes being desirable, depending on whether the implant is to be used as a stent, conduit or graft in connection with a large physiologic channel (e.g., the aorta) or a small channel (e.g., the vas deferens). Typically, the length of the implant will be between about 2 millimeters and about 10 centimeters, with this dimension, again being selected by the surgeon, according to the implant site where said implant is to be employed.

The structure of the implant may include a tube which is completely demineralized, a tube which has segments that are demineralized and segments that are not demineralized or which are partially demineralized, or an implant wherein only a portion thereof has a lumen therethrough. It will be recognized that the degree of demineralization dictates the level of implant flexibility, are required for particular physiologic applications or functions. In embodiments that are only partially demineralized, the advantage of increased radial strength and resistance to displacement, (radial tension), are achieved respectively due to portions of the implant that are retained in a mineralized state and the partially demineralized segments. This is important, for example, in cases where the implant is used as a stent to open an occluded blood vessel, or to prevent restenosis of an infarcted vessel. Another such application, for example, where radial rigidity would be advantageous, would be the use of the implant as a stent to prevent collapse of the urethra due to an enlarged prostate. The advantages of increased longitudinal flexibility are achieved as a result of those portions of the implant that are demineralized. Longitudinal flexibility allows the implant to traverse convoluted vessels or passageways, and permits retention of the implant in restricted passageways which are dilated to permit insertion of the relatively rigid portions of the implant. Upon release of the dilation, the flexible portion of the implant is "pinched" by the vessel to retain the implant at its implant site.

It will be recognized by those skilled in the art that the radial tension provided by the implant of this invention is a function of several features of the graft, stent or conduit, including: the wall thickness; the total architecture of the device (i.e. its overall shape, length and diameter); and the level of demineralization of each portion of the implant. In addition, it should be recognized that the wall thickness of the implant frequently has to be balanced between the desired level of radial tension that it can provide, the flexibility of the device that is required, and the internal and external diameter requirements of the passageway to which the graft, stent or conduit is to be applied.

Typically, for purposes of insertion into an existing physiologic channel, as opposed to joining to the end of such a channel which is also contemplated herein, the implant of this invention is prepared such that upon compression, the graft, stent or conduit has an outer diameter that is smaller than the internal diameter of the vessel, channel or conduit into which it is to be inserted. Upon decompression of the implant, or in its resting state, the implant has an outer diameter that is preferably slightly larger than the internal diameter of the physiologic channel into which the implant has been inserted, such that resulting friction and elastic forces assist in retaining the graft, stent or conduit at the implant site. In the case of a coil-shaped embodiment of this invention, it is possible to insert the implant into small and even convoluted vessels, and upon insertion, the implant adopts or retains a tubular structure that resists dislocation from its implant site.

In use, the implant of this invention is applied to ameliorate a wide variety of pathophysiologic conditions. For example, the implant may be inserted into the aorta as a stent to control the ballooning of aneurysms. Smaller diameter implants may be applied as vascular grafts to achieve coronary artery bypass. Peripheral vascular obstructive diseases, such as atherosclerosis, are ameliorated by expanding the lumen of the obstructed vessel using the implant of this invention. Esophageal, tracheal and intestinal grafts according to this invention may be used to replace portions of the esophagus, trachea, bronchi, or intestine that are removed, for example, to control cancerous growth, to control hernias, aneurysms, arterio-venous malformations (AVM's), or ulcers. Urinary, renal and biliary strictures are addressed by insertion of an appropriately sized stent according to this invention.

Those skilled in the art will recognize that where the term "stent" is used to describe the implant of this invention, the implant need not be fluid-impermeable (i.e. it may contain holes, slots or spaces throughout, so long as the radial strength is sufficient to allow the implant to act in opening up occluded vessels). Where the term "graft" is used, those skilled in the art will recognize that this implies that a portion of a physiological passage is replaced or interconnected to other such passages by means of the implant. Typically, when used as a graft, the device of this invention should be fluid impermeable, (e.g. as when the implant is used as a vascular graft), although this may not be absolutely required for all applications of the graft of this invention. Where the term "conduit" is used, those skilled in the art will appreciate that use of the implant of this invention is intended to create a passage through which physiologic processes may be directed (e.g. as in neural growth, which has heretofore been conducted through various conduits, see U.S. Pat. Nos. 5,026,381; 5,019,087; 4,963,146, all of which are hereby incorporated by reference). Such conduits may be fluid permeable, fluid impermeable, or semi-permeable, depending on the particular application requirements.

Stents according to this invention are inserted via an appropriate means known in the art, such as a catheter, to strengthen a weakened vessel, for example in an aneurysm, or to open an occluded vessel, as in coronary artery stenosis. Known techniques for stent implantation may be used for the instant device, as in, for example, the balloon expandable stents known in the art as those of PALMAZ-SCHATZ® (see, for example, U.S. Pat. Nos. 5,195,984; 5,571,171; 4,776,337; 5,102,417, hereby incorporated by reference), by use of balloon expansion of vessels and insertion of the implant of this invention, by use of catheters, by surgical insertion, and the like. Grafts according to this invention may be sutured in place according to methods known in the art, as for example in coronary artery bypass surgery (e.g. open heart sternotomy), either by suturing the demineralized or partially demineralized portion, or by passing sutures around nondemineralized, relatively rigid portions of the implant, which is inserted within or attached onto the end of an existing physiologic vessel or conduit. Other means known in the art, as in use of fibrinogen "glues", use of staples, laser technology, and the like may, of course, likewise be used to affix the grafts as needed. Linear grafts, tubular grafts, bifurcated grafts, and various other conformations suggested to those skilled in the art by the specific structures disclosed herein come within the scope of this invention. Conduits and uses therefore, such as in nerve regeneration, may likewise be provided and affixed as described for the stent and graft embodiments of this invention.

Referring to FIG. 1, there is provided a side view of a tubular implant embodiment 100 of this invention comprising a lumen and a body comprised of uniformly demineralized cortical bone (FIG. 1A) and an embodiment 100' wherein terminal annular segments of the implant are retained in a relatively rigid, mineralized or only partially demineralized state (FIG. 1B). The external features of the implant are machined to any desired shape prior to demineralization, and the lumen is likewise machined to any desired dimensions. In the implant 100, the implant has termini 101 and 102, a body 103 comprised of demineralized bone, a central bore 104, which creates a lumen 105 running through the implant between the termini 101, 102, or optionally, running only through a portion of the body of the implant 100. The implant 100 is prepared by machining a segment of cortical bone to achieve a tubular structure, according to methods known in the art. A central bore 104 is either machined through at least a portion of the implant body to provide the lumen 105, or the bore 104 may originate from a natural lumen structure, as in the natural intra-medullary canal that exists in certain bones, from which the marrow may be removed and which may be machined or otherwise treated to achieve a desirable lumen 105 diameter and surface. The entire implant body, or a portion thereof, is then demineralized according to methods known in the art, including but no limited to acid treatment to leach the minerals from the various portion of the implant sought to be demineralized.

In the embodiment 100' shown in FIG. 1B, the additional feature is provided wherein terminal segments 106, 107 of the implant are retained in a relatively rigid, mineralized or partially demineralized state. This feature provides a segment of the implant that acts to provide strength to the implant and a means for assisting in retention of the implant in place upon implantation. Alternatively, sutures may be sewn around the terminal segments 106, 107 and into the pliant internal segment 103 of the implant body. In this way, the termini of the implant may be sutured to adjacent vessel ends, or if inserted within a vessel, the sutures may be used to retain the implant immobile at the implant site. The relatively rigid annular segments 106, 107 are less susceptible to being ripped, as compared to the pliant, demineralized segment of the implant. Naturally, those skilled in the art will appreciate from this disclosure that only one terminal segment may be mineralized, while the other may be demineralized. Alternatively, both termini may be demineralized, and an internal portion or several discrete internal portions of the implant may be retained in a relatively rigid, mineralized or partially demineralized state. Examples of such embodiments are discussed in further detail below.

FIG. 2 provides a side view of a tubular implant embodiment 200 of this invention comprising termini 201, 202, a terminal bore 204, a lumen 205 and a body 203 comprised of cortical bone having demineralized longitudinal segments 210, 211, (FIG. 2A); those skilled in the art will recognize that it is a matter of application that defines the extent of demineralization and rigidity that is desired. Accordingly, the segments shown as 210, 211, may just as well be the mineralized segment, with the remainder of the implant being demineralized. Also shown, (FIG. 2B), is an embodiment 200' wherein, in addition, an internal segment 220 of the implant is fully demineralized while terminal annular segments 206, 207 of the implant are retained in a relatively rigid, mineralized or partially demineralized state (FIG. 2B), for a similar purpose and effect, as described above in regard to embodiment 100'. As noted above, in addition, the segment 220 may be the segment of the implant that is retained in the relatively rigid, mineralized or partially demineralized state, while the terminal segments 206, 207 may be the segments that are rendered pliable through demineralization.

FIG. 3 provides a side view of a tubular implant embodiment 300 of this invention comprising a terminal bore 304, a lumen 305, termini 301, 302, and a body 303 comprised of demineralized cortical bone wherein an annulus thereof, 320, between the termini of the implant, is retained in a relatively rigid, mineralized or partially demineralized state, (FIG. 3A). The width 310 of the annulus may be any desired width, so as to provide an internal relatively rigid segment that provides radial strength, sufficient to retain a desired internal diameter for a vessel which, in the absence of the implant, may be occluded. In an alternate embodiment 300', (FIG. 3B), the annulus of mineralized bone 320' is discontinuous, having segments of demineralized bone 330 interrupting the continuity of the mineralized annulus 320', thereby enhancing flexibility, while retaining radial strength. The width of the annulus, 310', may again be of any desired dimension.

FIG. 4 provides a sectional view through a tubular implant embodiment 400 of this invention comprising a lumen 404 and a body 403 comprised of a longitudinal segment 402 of demineralized cortical bone along one longitudinal aspect of the mineralized wall 401 of the implant (FIG. 4A). In a further embodiment 400', the implant comprises two longitudinal demineralized segments 402 along two longitudinal aspects of the implant (FIG. 4B). These sectional views are representative of the cross sectional composition of the implants shown in FIG. 2. The significance of the longitudinally demineralized segments of these embodiments is that they provide compressive flexibility to the implant which otherwise is longitudinally rigid due to the mineralized body of the implant. This feature would be helpful, for example, where the implant must be compressed in order to hold the stent, graft or conduit of this invention in its correct position and alignment within a vessel into which it is inserted.

FIG. 5 provides side views of implant embodiments 500, 500' having complex webbed (FIG. 5A) or striated (FIG. 5B) patterns of demineralized bone on an implant body that is substantially retained in a mineralized state. These implant embodiments are useful in specific applications such as replacement of tracheal segments, where a considerable amount of rigidity is required at the same time that flexibility is also necessary, or where a long lesion exists within a vessel, requiring a stent with a large surface area, strength, and flexibility. To this end, in a further embodiment of this invention, the implant may have a coiled structure (see FIG. 5C), which in a resting state, has a tubular structure, 500". In this embodiment, a segment of bone, having a diameter A, is machined in such a fashion that a spiral cut 505 in the bone is effected, the thus machined bone is then demineralized, allowing for extension of the implant into an extended, thin, coiled implant, 500'" (see FIG. 5D), having a smaller diameter B, and which has the natural tendency to retract into a tubular structure, having the diameter A. Depending on the degree of demineralization of this embodiment of the implant, increasing levels of strength and flexibility may be retained in all or defined parts of the implant.

In all of the above described embodiments of the implant of this invention, cortical bone segments are machined to the desired proportions, a lumen is drilled through at least a portion of the implant (unless the source bone already has an acceptable lumen or canal running through at least a portion thereof and which may be machined, as needed, to the desired proportions), and then portions of the implant are demineralized by treatment with, for example, 0.5 to 0.75 N hydrochloric acid, EDTA, or other leaching solvents known in the art. Treatment of the bone with waxy barriers, solvent impervious protective layers and the like are employed to achieve even the most complex of demineralization patterns. In addition, it will be appreciated by those skilled in the art that bone segments having a natural bore running therethrough, as with the intramedullary canal of the femur, tibia, fibia and the like, may be harvested and further machined to provide the appropriate shapes and dimensions as described herein after removal of bone marrow. Such bone sources are limited to production of conduits, however, which have rather large internal and external diameters, and may therefore be used only for provision of stents, grafts or conduits for some of the larger physiologic passages, such as the intestine, aorta and the like. Smaller segments of bone are therefore machined to provide the lumen where smaller internal and external diameter grafts, stents or conduits are required, and where appropriate, such machining may be achieved by drilling and the like, or by use of an appropriate laser.

Figure 5E:
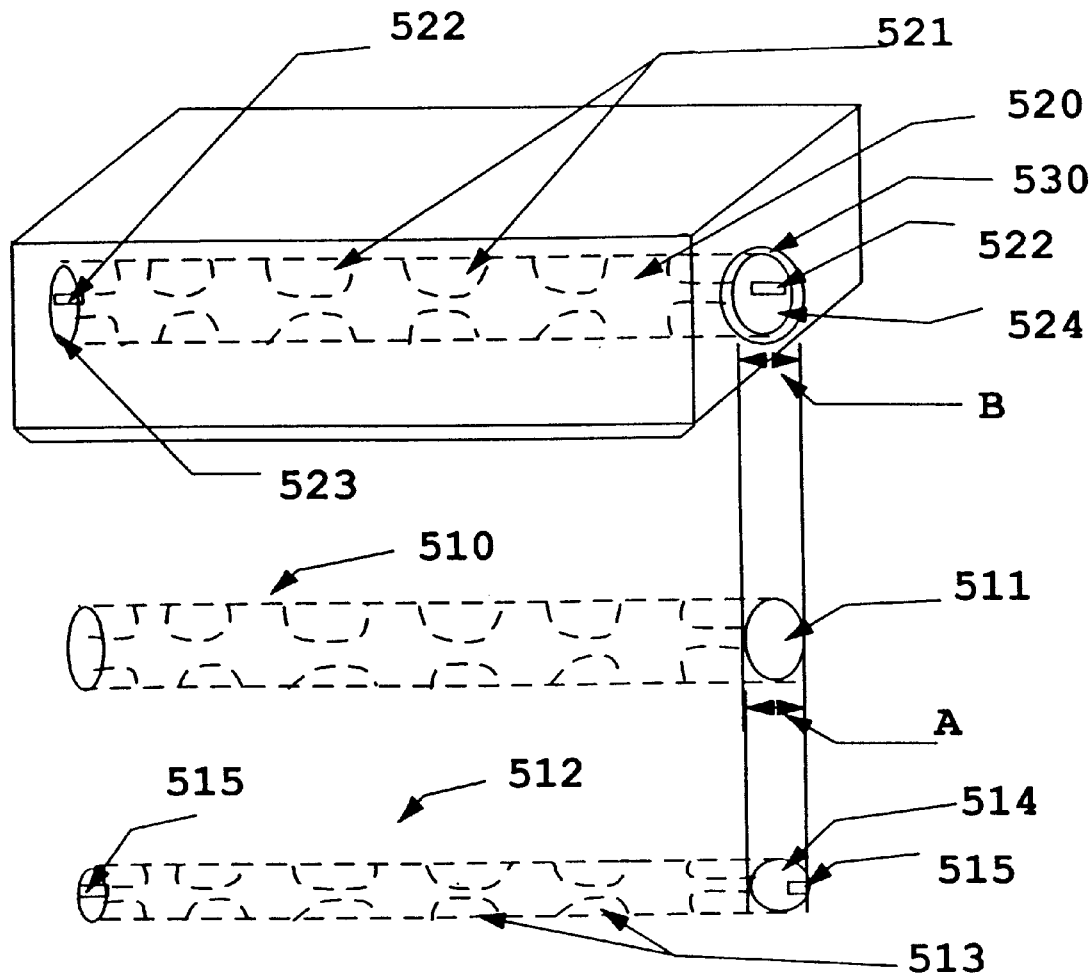
FIG. 5 provides side views of implants having complex webbed (FIG. 5A) or striated (FIG. 5B) patterns of demineralized bone on an implant body that is substantially retained in a mineralized state. In a further embodiment (FIGS. 5C and 5D), a "coiled" structure for the implant is shown.

To provide variegated patterns of demineralization, as shown in FIGS. 5A and 5B, a novel device and demineralization method, exemplified in FIG. 5E, may be employed. According to this method, a segment of bone machined to desired proportions of length, and diameter to form the implant 510, including a lumen 511, is adapted with a tightly-fitting, internal tube 512, made from a fluid impermeable material (plastic, silicone, polyethylene, and the like), having defined therein a pattern 513 cut into and through the walls of the tube 512. The external diameter A of the inner tube is chosen to closely match (i.e. be slightly smaller than) the internal diameter A of the implant 510.

The shape of the cut-out pattern 513 matches the pattern which is intended to be transferred to the implant as a pattern of demineralization. The tube 512, has a bore 514, into which and through which demineralization solution, such as acid, may be made to flow. Upon fitting the tube 512 into the lumen 511 of the implant, passage of demineralization solution therethrough permits demineralization of the implant 510 from the inside, to create the desired demineralization pattern therein.

To make enhance the efficiency of the demineralization process, the pattern of demineralization may be imparted to the exterior of the implant 510 at the same time that the implant is partially demineralized from the inside. This is achieved by inserting the entire implant 510 with the tube 512 inserted therein into an outer tube 520. The internal diameter B of the outer tube 520 is selected such that it closely matches (i.e. is only slightly larger than) the external diameter B of the implant 510. This outer tube 520 is also made from a fluid impermeable material. A pattern 521, matching that cut out in the walls of the tube 512, is cut out into and through the walls of the tube 520. In order to keep the patterns of the tubes 512 and 520 in register with each other, at one or both ends of the tube 512, a registration means 515, including marks, grooves or projections, is provided which fit with a complementary registration means 522 provided in the outer tube 520. Accordingly, the implant carrying the internal tube 512 can only be inserted into the outer tube 520 in such an orientation as to cause the pattern 513 to align perfectly with the pattern 521. The implant 510 is also matched with an outer tube 520 such that a tight fit or seal is created between the external walls of the implant 510 and the internal walls of the tube 520. If needed, this seal may be enhanced by use of silicone caulk or the like. The outer tube 520 with the implant 510 inserted therein and having the internal tube 512 inserted therein is then inserted through a sealable aperture 530 of a demineralization bath 535. The bath 535 is filled with a demineralization solution, such as acid, and the pattern of demineralization is permitted to become defined for an appropriate length of time, defined by the thickness of the implant 510 and the strength of the demineralization solution. The interior of the the implant may be exposed to demineralization solution by keeping the end 523 of the implant open such that demineralization solution flows into the interior of the inner tube 512. The end 524 may be stoppered, or adapted with hose and a pump, which causes the demineralization to flow through the inner tube 512 and back into the demineralization bath 535. In this manner, any desired pattern of demineralization may be imparted to the implant. By adapting this method to various shapes of protective means, any type of demineralization may be defined in a bone implant of essentially any shape.

In order to provide conduits having branched or bifurcated structures, implant segments according to this invention are cut, sutured, or joined. FIG. 6 provides side views of various stages in the process of preparing a bifurcated implant 660 of this invention by slicing and suturing a demineralized segment of an implant 600 according to this invention. According to this method, the implant 600 is demineralized over the segment 610, while retaining a segment 620 in a mineralized state. Alternatively, the segment 620 may likewise be demineralized. In either case, the demineralized segment 610 is cut along a longitudinal axis of the implant (FIG. 6A), to produce an intermediate device (FIG. 6B) having two semi-detached segments 640, 650. Each semi-detached segment is folded upon itself and held in the folded state by sutures 690, or like means, to provide a bifurcated conduit 660 having two channels 680, 670 (FIG. 6C).

Figure 7:
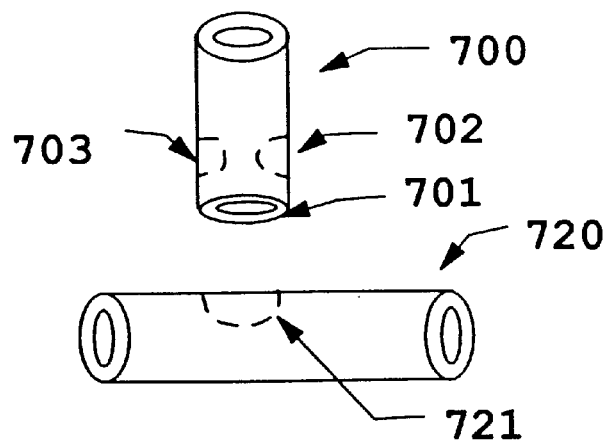
FIG. 7 provides side views of various stages in the preparation of bifurcated implants according to this invention by suturing compatible implant parts to each other (FIG. 7B), or by inserting one implant segment into another implant segment, and suturing the segments together (FIG. 7C).
Figure 7:
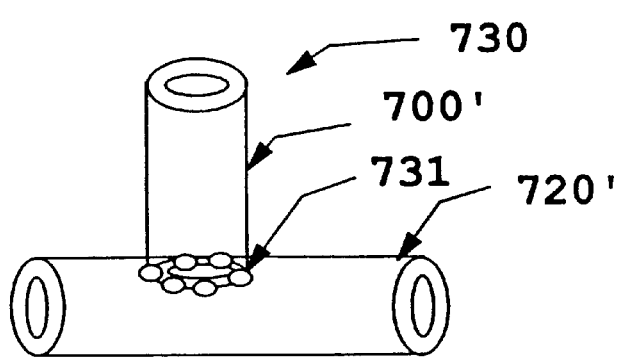
Figure 7:
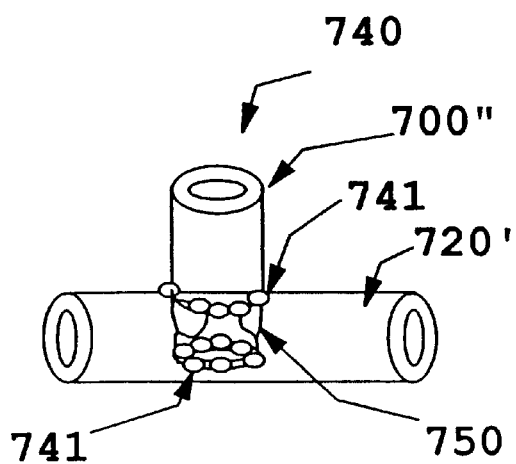

In another embodiment of this invention, bifurcated vessels 730, 740 are produced by implant segments 700, 720 of this invention. In one aspect, the implant segment 720 is cut to produce an entry-way 721 along a medial, demineralized aspect of the implant. The implant 701 is at least partially demineralized such that a terminal aspect 701 thereof is pliant. As shown in FIG. 7B, the thus prepared implant elements are then affixed to each other, by suturing or like means, to provide the bifurcated structure 730, composed of elements 700' and 720' connected at the entry-way 731 cut in element 720'. In an alternate method (FIG. 7C), side holes 702, 703 are cut into the implant 700 to produce element 700". Thus prepared, element 700" is inserted through the entryway 721 in element 720' and retained in place by sutures 741 or like means. In either embodiment, 730, 740, fluid, cells or other biological processes directed through conduit 720', are likewise directed through conduits 700' or 700".

Figure 8:
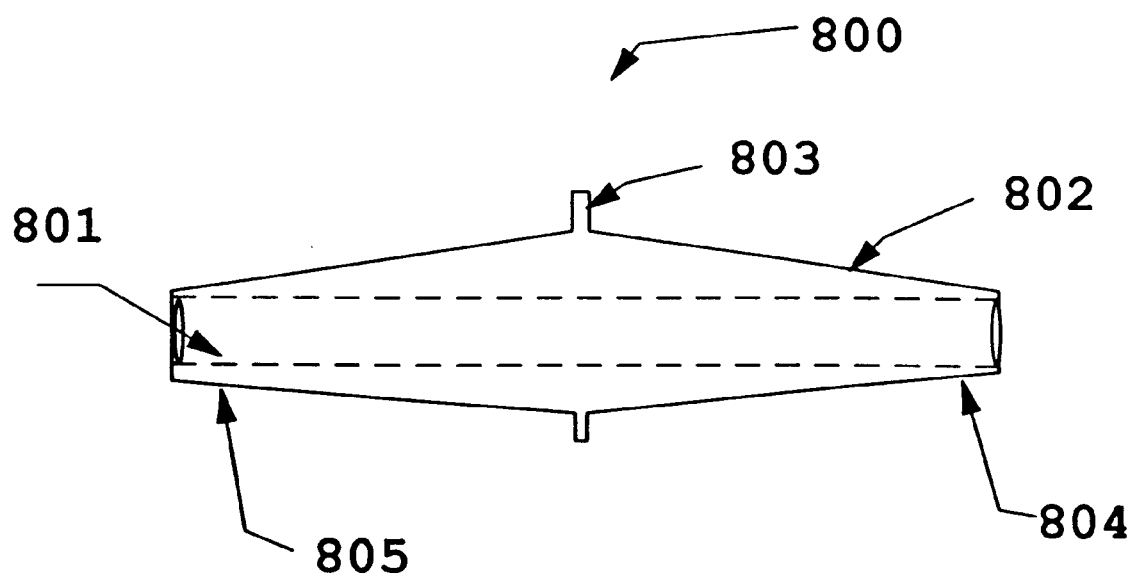
FIG. 8 shows a device of this invention for use as a lumen junction means.

In FIG. 8, a device 800 according to the present invention, for use as a conduit or a junction means, is disclosed. This device has a similar structure and purpose to a device disclosed in U.S. Pat. No. 5,139,505 for suturing hollow organs. However, the present device is made from a distinct material and by the distinct method of the present invention and is therefore much different to the device of the referenced patent. Per the present invention, a portion of cortical bone is machined to exhibit an inner surface 801 an outer surface 802 with frusto-conical ends, and an intermediate rim 803. The ends 804, 805 of the device 800 may be demineralized to provide flexibility which may aid in insertion of the ends 804, 805 into the adjacent lumen of vessels, including blood vessels or other existing physiologic conduit, to be joined, while the rim 803 may be retained in a relatively rigid, mineralized or partially demineralized state. Alternatively, the ends 804, 805 may be retained in a relatively rigid mineralized or partially demineralized state, while the rim 803 may be demineralized or partially demineralized. Variations on the basic structure disclosed herein are, likewise, contemplated by the present invention, such as for example, provision of a series of holes around the periphery of the rim 803, through which sutures in the adjacent ends of the vessels to be joined are passed, thereby affixing the vessel ends to the rim 803 of this embodiment of the device of this invention.

Those skilled in the art will recognize that in any of the above described embodiments of this invention, various treatments may be applied to the implant to reduce antigenicity or immunogenicity, by tanning with glutaraldehyde, treatment with azide, or the like, to reduce thrombogenicity, by coating of the implant with collagen, siloxane (and the like surface treatments, to reduce porosity), immunologically acceptable cells or cell products or by culturing the implant in the presence of such cells as fibroblasts, sertoli cells, endothelial cells or smooth muscle cells, or the like, and to increase bioactivity, as in coating or soaking the graft, conduit or stent of this invention with growth factors, or phospholipids, and the like or culturing the implant with sertoli cells to enhance neural growth, culturing the implant with endothelial cells, to provide a conduit acceptable for implantation in the lumen of the intestine, or culturing the implant with smooth muscle cells, to provide a contractile cellular surface to the implant.

Having generally and specifally described the implant of this invention, including its best mode, the invention to which an exclusive right is claimed is set forth in the claims which

What is claimed is:

1. An implant comprising a luminal graft, stent or conduit for implantation in or connecting portions of a body part having a lumen or at a physiologic location where the presence of a conduit is beneficial, wherein said implant comprises a segment of cortical bone, said bone segment comprising a bore or lumen running through at least a portion thereof, and wherein at least a portion of said segment of cortical bone is demineralized such that said segment is flexible said implant configured to be implanted within or connecting one or more blood vessels, ducts, or passages.

2. The implant of claim 1 configured to be implanted within or connecting one or more blood vessels.

3. The implant of claim 2 wherein said one or more blood vessels is a vein, or an artery.

4. The implant of claim 1 configured to be implanted within or connecting one or more ducts, vessels or passages.

5. The implant of claim 4 wherein said one or more ducts or passages are selected from a bile duct, an hepatic duct, a renal duct, an urethral duct, an ureter, a vas deferens, a fallopian tube, an exocrine glandular duct, a lymphatic duct, the esophagus, the trachea, a bronchial passage, and the intestine.

6. The implant of claim 1 having an inner surface, an outer surface, with frusto-conical ends, and an intermediate rim.

7. The implant of claim 6 wherein said ends are demineralized to provide flexibility in insertion of the ends into the adjacent lumen of vessels to be joined and said rim is retained in a relatively rigid, mineralized or partially demineralized state, or wherein said ends are retained in a relatively rigid mineralized or partially demineralized state and said rim is demineralized or partially demineralized, or wherein said implant is demineralized or partially demineralized throughout.

8. The implant of claim 1 configured to be implanted between the ends of a severed nerve so as to provide a conduit for neural growth.

9. The implant of claim 1 having a tubular, coiled or bifurcated structure said implant configured to be implanted within or connecting one or more blood vessels, ducts, or passages.

10. The implant of claim 1 having a collagen coating, a siloxane coating, a cellular coating, having been treated with growth factors or phospholipids or having been cultured with a specific cell type.

11. The implant of claim 10 configured to be cultured with sertoli cells.

12. The implant of claim 10 configured to be cultured with endothelial cells.

13. The implant of claim 10 configured to be cultured with smooth muscle cells.

14. The implant of claim 1 comprising a tube of uniformly demineralized cortical bone having a natural lumen or a lumen machined therein said implant configured to be implanted within or connecting one or more blood vessels, ducts, or passages.

15. The implant of claim 1 comprising at least one terminal segments retained in a mineralized state and at least one internal demineralized segment, or at least one terminal segment that is demineralized and at least one internal segment that is retained in a mineralized or partially demineralized state.

16. The implant of claim 1 having at least one longitudinally demineralized segment said implant configured to be implanted within or connecting one or more blood vessels, ducts, or passages.

17. The implant of claim 16 comprising terminal segments that are retained in a mineralized state.

18. The implant of claim 1 comprising a tube of demineralized bone having a lumen and at least one internal relatively rigid annulus or segment, circumferentially complete or incomplete, of mineralized bone.

19. The implant of claim 1 comprising a tube of bone having a lumen wherein said bone has a webbed, coiled or striated pattern of demineralized segments.

20. The implant of claim 1 wherein at least a portion thereof is radiopaque.

21. The implant of claim 1 configured to be treated so as to have a reduced antigenicity, immunogenicity, or thrombogenicity.

* * * * *